United States Patent [19]

Neumeyer

[11] 4,353,912
[45] Oct. 12, 1982

[54] N-HALOALKYL NOR APOMORPHINES AND METHOD OF INACTIVATING DOPAMINE RECEPTOR SITES AND ENHANCING DOPAMINERGIC ACTIVITY THEREWITH

[75] Inventor: John L. Neumeyer, Wayland, Mass.

[73] Assignee: Northeastern University, Boston, Mass.

[21] Appl. No.: 147,737

[22] Filed: May 8, 1980

[51] Int. Cl.³ .................... A61K 31/47; C07D 221/18
[52] U.S. Cl. .................................... 424/258; 546/75; 546/2; 546/3; 546/13; 424/245; 424/254; 544/299
[58] Field of Search ........................... 546/75; 424/258

[56] References Cited
U.S. PATENT DOCUMENTS 3,717,639  2/1973  Neumeyer .............................. 546/75
3,717,643  2/1973  Archer .................................. 546/75
3,852,452  12/1974  Bruderlein et al. ...................... 546/75

Primary Examiner—David B. Springer
Attorney, Agent, or Firm—Weingarten, Schurgin & Gagnebin

[57] ABSTRACT

N-substituted haloalkyl apomorphines of the formula

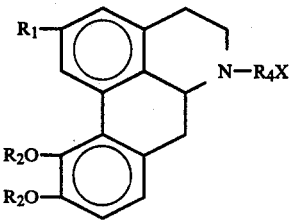

wherein $R_1$ is hydrogen or $R_2O$; $R_2$ is hydrogen, acyl, lower alkyl or

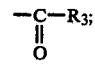

$R_3$ and $R_4$ are lower alkyl; and X is halogen; and their acid addition salts. Representative compounds have neuroleptic properties.

4 Claims, 8 Drawing Figures

INDUCTION OF CIRCLING IN RATS

INHIBITION OF CIRCLING IN MICE PREVIOUSLY CHALLENGED WITH APOMORPHINE

INHIBITION OF CLIMBING IN MICE PREVIOUSLY CHALLENGED WITH APOMORPHINE

EFFECT OF WASHING ON THE BINDING OF (-)N-(2-CHLOROETHYL)NORAPOMORPHINE. HCl (NCA) AND OF (-)N-(2-HYDROXYETHYL)NORAPOMORPHINE. HCl (NHA) TO RAT STRIATAL HOMOGENATE

IN VIVO EFFECT OF THE INTRASTRIATAL BINDING OF
(N)-(2-CHLOROETHYL)NORAPOMORPHINE. HCl ON SUBSEQUENT
BINDING OF $^3$H-N-n-PROPYLNORAPOMORPHINE ($^3$H-NPA)

IN VITRO EFFECT OF THE INTRASTRIATAL BINDING OF
(N)-(2-CHLOROETHYL)NORAPOMORPHINE, HCl ON SUBSEQUENT
BINDING OF $^3$H-N-n-PROPYLNORAPOMORPHINE ($^3$H-NPA)
ALONE OR IN PRESENCE OF OTHER BLOCKING AGENTS

N-HALOALKYL NOR APOMORPHINES AND METHOD OF INACTIVATING DOPAMINE RECEPTOR SITES AND ENHANCING DOPAMINERGIC ACTIVITY THEREWITH

This invention relates to novel N-substituted haloalkyl apomorphines having the formula

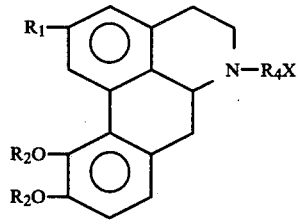

wherein $R_1$ is hydrogen or $R_2O$; $R_2$ is hydrogen, acyl, lower alkyl or

$R_3$ and $R_4$ are lower alkyl; and X is halogen. Acid addition salts of these apomorphines are also included.

A representative compound of this class, i.e., (−)-N-(2-chloroethyl)norapomorphine.HCl, has been shown to be able to abolish dopamine agonist action and confer dopamine antagonist potential as assessed behaviorally and biochemically. These compounds are therefore potentially useful as neuroleptic drugs in treating psychoses.

Neuroleptic drugs such as phenothiazines, thioxanthenes and butyrophenones, are used in the treatment of psychoses to counteract hallucinations and delusions, and to alleviate psychomotor excitement and assaultiveness. In this role, these drugs reduce dopaminergic activity to the central nervous system by blocking the dopamine receptors, thus preventing the activation of adenylate cyclase identified as the agent responsible for the conversion of adenosine triphosphate (ATP) to cyclic adenosine monophosphate (cyclic AMP), a nucleotide. The generation of cyclic AMP within a brain cell is believed to stimulate the cell. In treating psychoses, e.g., schizophrenia, it has been found that drugs that act as antagonists of the dopamine receptor are effective, indicating that schizophrenia results from an overactivity of dopamine-containing neurons in certain areas of the brain. Thus by controlling such dopamine-containing neurons it is possible to control psychoses.

A number of different neuroleptics are currently prescribed. Typical of the phenothiazines is chlorpromazine hydrochloride

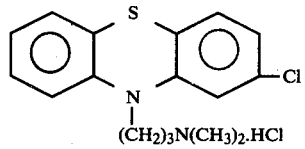

Although this drug is an effective neuroleptic, it must be given as often as three times daily at relatively large dose levels (200 to 800 mg/day); and it has such side effects as sedation, extrapyramidal activity, and the inducing of hypotension.

Chlorprothixene having the formula

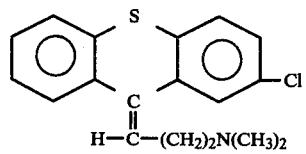

is representative of the thioxanthenes. Like chlorpromazine, it must be given often at a dosage level of from 50 to 400 gms/day and has essentially the same side effects.

The butyrophenones, represented by haloperidol having the formula,

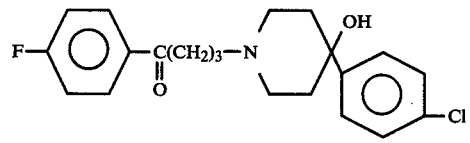

have high neuroleptic potency. Haloperidol produces a high incidence of extrapyramidal reactions; but it has less sedative effect, less prominent antonomic effects and less hypotensive effect than the phenothiazines. Dosage levels for the butyrophenones range from 2 to 6 mg/day.

As will be seen, these three classes of compounds now in use as neuroleptics are chemically distinguishable from the N-substituted haloalkyl norapomorphines of this invention; and therefore it is not apparent that compounds having a structure totally different from the known neuroleptics could be effective in that role. Moreover, apomorphine and its homolog N-propylnorapomorphine are known as drugs which act by directly stimulating the dopamine receptors. (See G. C. Cotzias, P. S. Papavasieron, E. S. Tolosa, J. S. Mendez and M. Bell-Miduron, N. Eng. J. Med. 294:567 (1976).) Thus, whereas apomorphine and N-propylnorapomorphine are recognized as dopamine receptor agonists, the N-substituted haloalkyl norapomorphines of this invention are dopamine receptor antagonists.

As will be described below in detail, the compounds of this invention are believed to provide dopaminergic activity through binding with the dopamine receptors, thus providing a mechanism different from that exhibited by the currently administered neuroleptic drugs which are blocking agents, and offering advantages over them.

It is therefore a primary object of this invention to provide a novel class of N-substituted haloalkyl noraporphines. Another object is to provide compounds of the character described which exhibit greater dopaminergic activity than the neuroleptic drugs presently in use. A further object of this invention is to provide such neuroleptic drugs which are longer-acting and hence require administering less frequently than such drugs as chlorpromazine, chlorprothixene or haloperidol. Yet another object is to provide a dopaminergically active compound which inactivates dopamine receptors by binding to them rather than by blocking them.

Another primary object of this invention is to provide a method for controlling psychoses. A further object is to provide a method of the character described which provides such control over a time period greater than now possible with the neuroleptic drugs presently in use.

Other objects of the invention will in part be obvious and will in part be apparent hereinafter.

The invention accordingly comprises the several steps and the relation of one or more such steps with respect to each of the others and the compounds possessing the characteristics, properties and the relation of components which will be exemplified in the compounds hereinafter described, and the scope of the invention will be indicated in the claims.

Accordingly to one aspect of this invention there is provided a compound having the formula

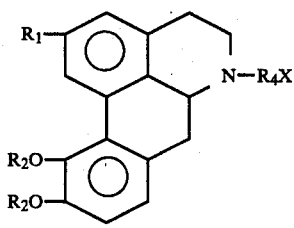

wherein $R_1$ is hydrogen or $R_2O$; $R_2$ is hydrogen, acyl, lower alkyl or

$R_3$ and $R_4$ are lower alkyl, and X is halogen; and the acid addition salts thereof.

According to another aspect of this invention there is provided a method of controlling psychoses by administering a therapeutically effective amount of (—)N-(2-chloroethyl)norapomorphine, or the HCl addition salt thereof, to a patient in need of such treatment.

For a fuller understanding of the nature and objects of this invention, reference should be had to the following detailed description taken in connection with the accompanying drawings in which FIG. 1 illustrates a reaction scheme for synthesizing an exemplary compound of this invention;

As used hereinafter, the term "lower alkyl" means saturated, monovalent alphatic radicals including straight and branched-chain radicals of from one to six carbon atoms, as illustrated by, but not limited to methyl, ethyl, propyl, isopropyl, butyl, sec. butyl, amyl, hexyl and the like.

As used hereinafter, the term "acyl" means an organic radical derived from an organic acid by the removal of the hydroxyl group.

Figure 1:
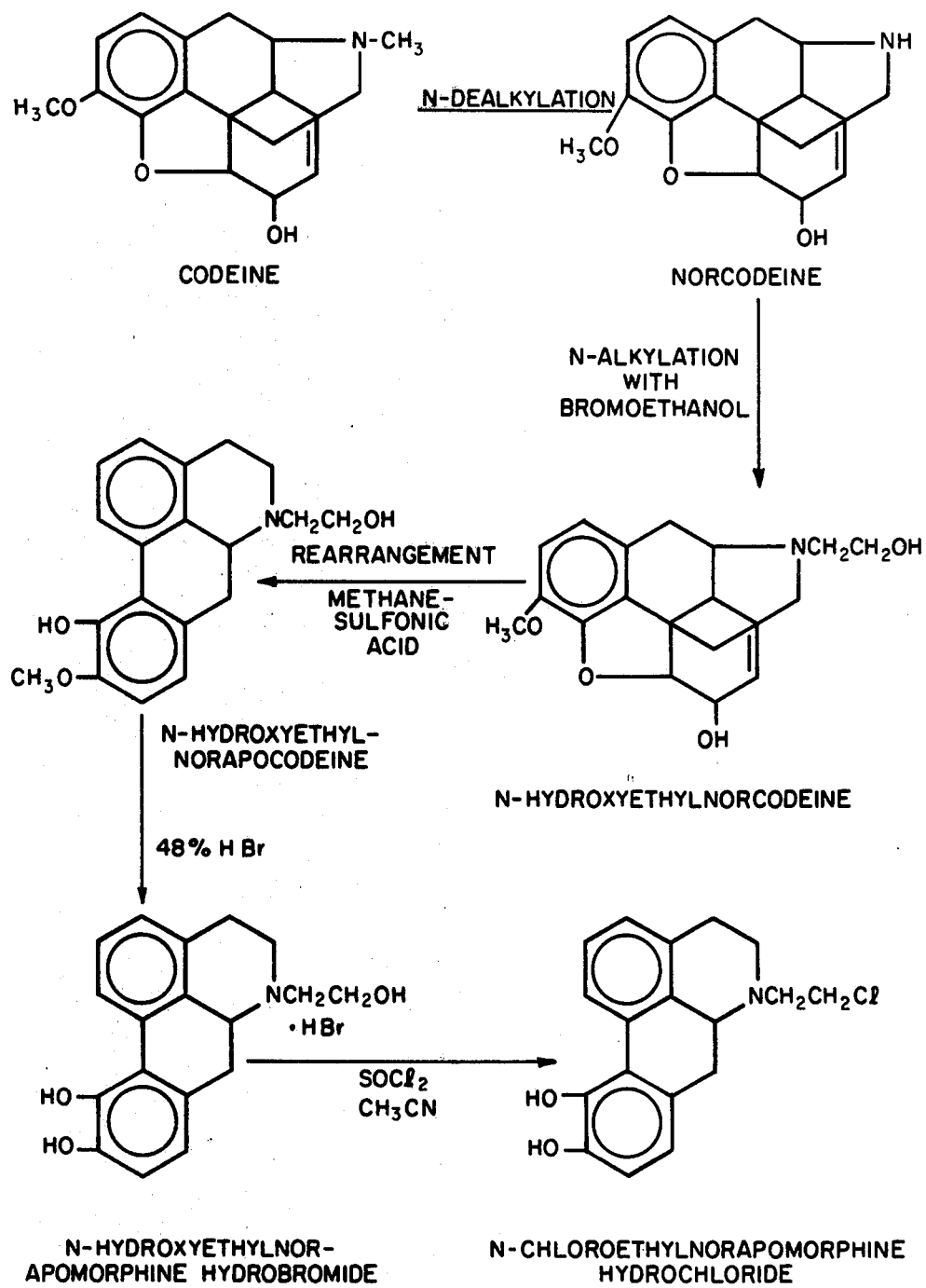

FIG. 1 is an exemplary reaction scheme for synthesizing (—)N-chloroethyl)-10,11-dihydroxynorapor-phine.HCl (NCA), the prefered form of the neuroleptic drugs of this invention. As will be seen from FIG. 1, this synthesis begins with the N-demethylation of codeine to norcodeine, such as by the methods described by M. M. Abdel-Monem and P. S. Portoghese (J. Med. Chem: 15, 208 (1972)) or by K. Rice (J. Org. Chem: 40, 1850 (1975)). Subsequent N-alkylation of the norcodeine with bromoethanol is followed by the rearrangement of the resulting N-hydroxyethylnorcodeine with methanesulfonic acid to give the N-hydroxyethyl-norapocodeine, using the procedure of F. E. Granchelli, C. N. Filer, A. H. Soloway and J. L. Neumeyer (J. Org. Chem: in press (1980)). Treatment of the N-hydroxyethylnorapocodeine with 48% hydrogen bromide at 120°–135° C. under nitrogen for at least 2 hours effects dealkylation to form N-hydroxyethylnorapomorphine hydrobromide which is then converted to the hydrogen chloride salt by neutralization of the reaction mixture with ammonium hydroxide, followed by extraction and then treatment of the resulting free base with ethereal HCl. Finally, treatment of this acid addition salt with thionyl chloride and acetonitrile at room temperature yields the desired (—)N-chloroethyl)-10,11-dihydroxynoraporphine after neutralization of the evaporated reaction mixture with ammonium hydroxide. The hydrogen chloride salt is prepared from an ethereal HCl extract, mp 173°–178° C.

NMR and UV spectra as well as elemental analysis are used to establish the structure of the compound. NMR of the free base (MeOH-d$_4$) δ 2.33–4.40 (broad signals, 13, H at C-4, C-5, C-6a, C-7, NCH$_2$CH$_2$Cl and phenolic OH) 6.53–7.40 (m, 4, aromatic), 8.1–8.37 (dd, 1, aromatic H at C-1); MS, m/e 315 (M+), 266 (base); UV$_{max}$ (EtOH) 275 nm, (log ε, 4.169); [α]$_{Hg}^{28546}$ −35°. Anal. Calcd for C$_{18}$H$_{23}$NO$_3$Cl(MW 336.82): C, 55.68; H, 5.97; N, 3.60. Found: C, 55.96; H, 5.34; N, 3.59.

Using well-known techniques the free base and acid addition salts may thus be converted from one form to the other and one acid addition salt may be converted to another by regenerating the free base form and acidifying it.

Appropriate acid addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benezenesulfinic acid, p-toluenesulfonic acid, benzenesulfinic acid, butylarsonic acid, diethylphosphinic acid, p-aminophenylarsinic acid, phenylstibnic acid, phenylphosphinous acid, methylphosphinicacid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The following examples, which are meant to be illustrative and not limiting, provide further details with regard to the synthesis of the N-substituted-haloalkyl apomorphines of this invention.

EXAMPLE 1

(—)N-(2-hydroxyethyl)norapomorphine.HBr

A mixture of N-hydroxyethylnorapocodeine (2.51 grams, 8.06 mmole), prepared by the synthesis route described above, and 50 milliliters of 48% HBr was heated at 130° C. under nitrogen for four hours. The reaction mixture was cooled and then evaporated to a dry residue in vacuo. The resulting residue was recrystallized from methanol/ethyl ether to give an off-white solid (2.21 grams, 72%), mp 235°–238° C. TLC (precoated silica gel on polyethylene terephthalate foil) showed $R_f$ of 0.24 in ethanol/chloroform 1/9 volume).

EXAMPLE 2

(—)N-(2-chloroethyl)norapomorphine.HCl 1.0 milliliter of thionyl chloride was added dropwise to a mixture of (—)N-(2-hydroxyethyl)norapomorphine (0.50 gram free base, 1.7 mmole) in 10 milliliters of dry acetonitrile. The resulting solution was stirred at room temperature for 24 hours, evaporated to a residue in vacuo, diluted with 25 milliliters of water, neutralized with ammonium hydroxide and extracted with chloroform (3×25 milliliters). The combined extracts were dried ($Na_2SO_4$) and evaporated to a residue which was triturated with 50 milliliters of ethyl ether. The ethereal filtrate was treated with excess ethereal HCl to give a light green solid (0.38 gram, 64%), mp 173°–178° dec. TLC showed $R_f$ of 0.23 in ethyl acetate.

The (—)N-(2-chloroethyl)norapomorphine.HCl of Example 2 may be converted to the ester form wherein $R_2$ is

by heating with the appropriate $R_3COCl$. Thus diacetyl (—)N-(2-chloroethyl)apomorphine may be formed by heating (—)N-(2-chloroethyl)norapomorphine.HCl with acetyl chloride.

Apomorphine-induced behavioral characteristics in the rodent are considered to involve dopamine agonist action on striatal and mesolimbic dopamine receptors. Therefore, the ability of a drug to inhibit such apomorphine-induced behavior is considered a measure of the effectiveness of the drug to antagonize dopamine receptors and hence a measure of its dopaminergic activity. Among such induced behavioral characteristics are circling, climbing and stereotypy.

The observed ability of the N-substituted haloalkyl norapomorphines of this invention to inhibit striatal and possibly mesolimbic dopamine function over a period of days in contrast to a few hours for the phenothiazines and butyrophenones suggests that they bind irreversibly to the receptor rather than provide a temporary blocking action. Biochemical assays, reported below, show that the compounds of this invention are able to inhibit $^3$H-NPA ($^3$H-N-n-propylnorapomorphine) binding to rat striatal tissue. It is submitted that such inhibition is the result of the binding of the N-substituted haloalkyl norapomorphines to the dopamine receptor.

Male albino mice in the weight range of 35–40 grams were used in the determination of circling behavior. The mice were prepared for circling experiments using standard stereotaxic techniques to place unilateral electrolesions in the right caudate-putamen (1.0 mm anterior to bregma, 2.0 mm lateral and 3.5 mm below the skull surface, 1.5 mA/15 s). Fourteen days after the surgery the mice were challenged with 0.5 mg/kg apomorphine administered subcutaneously. Those mice circling less than 6 revolutions every 2 minutes were excluded from subsequent studies. Circling behavior was dose-dependent, 0.25–1 mg/kg apomorphine causing from 2–10 revolutions every 12 minutes. A doseage of 0.5 mg/kg apomorphine was selected for use in the drug interaction studies described. At this dosage level of subcutaneously administered apomorphine, the test animals circled from 6 to 8 revolutions/2 minutes.

Figure 2:
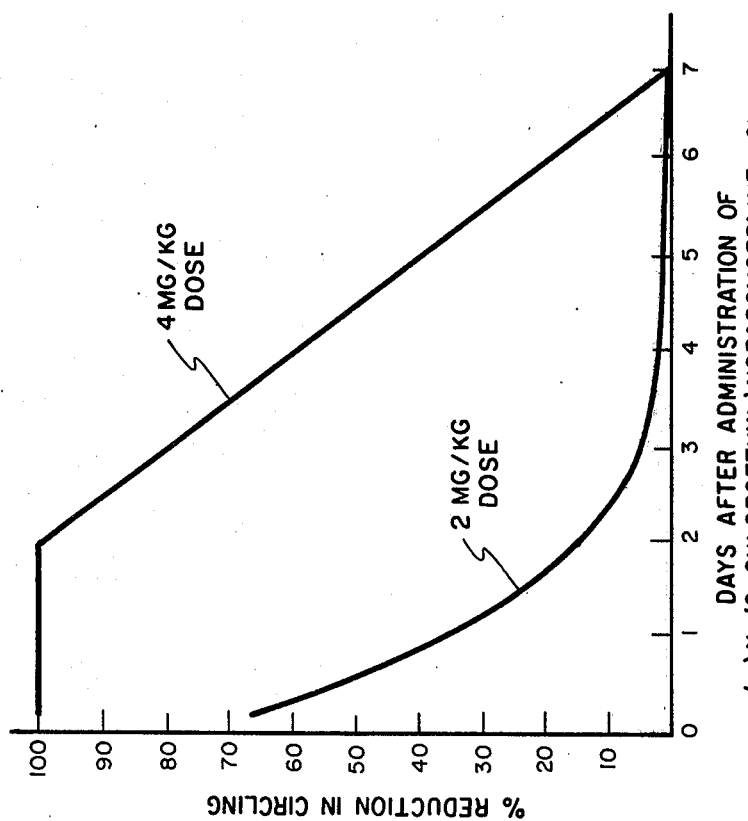
FIG. 2 is a plot illustrating the ability of (—)N-(2-chloroethyl)norapomorphine.HCl at two different dosage levels to inhibit circling in apomorphine-challenged mice.
Figure 4:
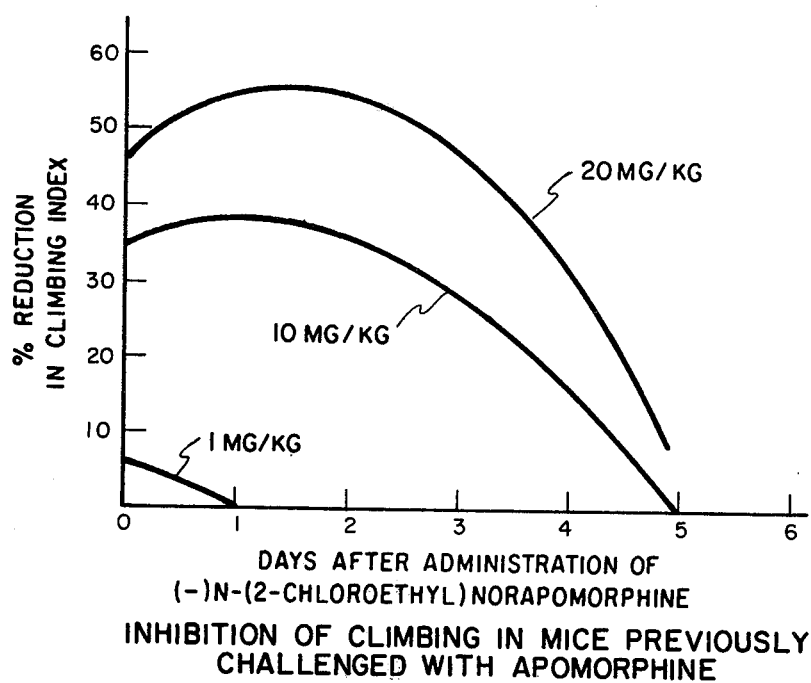
FIG. 4 is a plot illustrating the ability of (—)N-(2-chloroethyl)norapomorphine.HCl at different dosage levels to inhibit climbing in apomorphine-challenged mice.

The unilateral striatectomized mice antagonized by apomorphine were then given, by subcutaneous injection, doses of 1.0, 2.0 or 4.0 mg/kg of the (—)N-(2-chloroethyl)norapomorphine.HCl prepared in Example 2 and made up in a N,N-dimethylformamide/water solution. Circling in an open field was observed to determine the degree to which the circling was inhibited 4 hours and 2, 5 and 7 days after administration. At the lowest dosage level of 1.0 mg/kg, essentially no inhibition was noted; but as shown in the plots of FIG. 2, at the higher dosage levels, the reduction in circling was still apparent after 2 days and at the highest dosage level it was as much as 39% after 5 days. Thus these data clearly show that ipsilateral circling behavior induced in unilateral stratectomized mice by apomorphine, one of the most valuable models for indicating change in striatal dopamine function, could be abolished by the peripheral administration of the (—)N-(2-chloroethyl)-norapomorphine.HCl presumably by an action on striatal dopamine receptors in the "intact" hemisphere.

A further behavioral model utilized rats (male, Sprague-Dawley, 300±25 g). The (—)N-(2-chloroethyl)norapomorphine.HCl was injected unilaterally into the striatum of the rat and then it was determined whether a "dopamine blockade" had been achieved by subsequently challenging with apomorphine and measuring any circling induced. Bilateral guide cannulae were chronically implanted in the rats, using standard stereotaxic techniques, to allow drug/vehicle injection at the center of the caudate-putamen complex (Ant. 8.0, Lat. +3.0, Vert. +1.5, De Groot, 1959). Fourteen days after cannulation, the animals were manually restrained and the drug in a solvent vehicle was injected in a volume of 4 μliters (1 μliter/min) into the right and left striata, respectively. The 4 μliter contained dosages of 10 μg or 40 μg of the drug. Any body asymmetry or circling movements resulting from the intracerebral injections were noted, and subsequently any circling behaviour (measured in an open field as revolutions/minute) to challenge with 0.5 mg/kg subcutaneously administered apomorphine was measured on the second, fifth, seventh and fourteenth days following intrastriatal administration.

Figure 3:
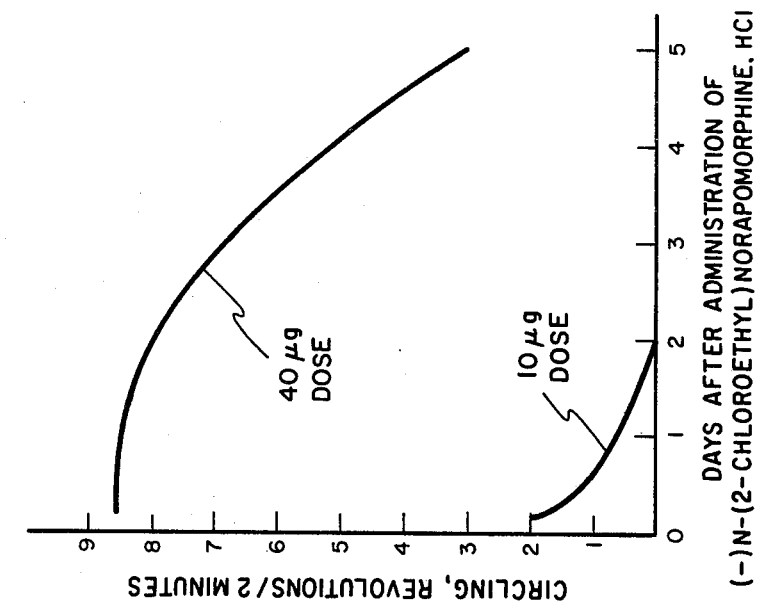
FIG. 3 illustrates the effect on rat circling of intrastriatal injections of (—)N-(2-chloroethyl)norapomorphine.HCl prior to treatment with apomorphine.

The unilateral injection of 10 and 40 μg of the (—)N-(2-chloroethyl)norapomorphine.HCl into the caudate-putamen induced ipsilateral asymmetry/circling movements within an hour of administration. The resting asymmetry was particularly evident when the animals were disturbed and was also noted two and five days after the injection of the (—)N-(2-chloroethyl)norapomorphine. By the seventh day the ipsilateral asymmetry was variable and was not apparent by the fourteenth day. The subcutaneous administration of apomorphine (0.5 mg/kg) enhanced the ipsilateral asymmetry and precipitated a clear circling behavior at the 40 μg dose of the drug four hours and two days, and to a lesser extent 5 days after its administration as shown in FIG. 3.

Thus it appears logical to conclude that the intrastriatal injection of the (—)N-(2-chloroethyl)norapomorphine in the rat caused a blockade of dopamine receptors at the site of injection since, if the injection was made into one hemisphere only, peripherally administered apomorphine caused rats to circle ipsilaterally to that side, which would again indicate a limitation of action to the "intact" hemisphere. Again, as in the circling experiments with the mice, it was apparent that the dopamine inhibitory actions of the drug endured for 2 to 4 days. The recovery of the behavioral response possibly reflects the resynthesis of dopamine receptors.

Climbing behavior was measured by placing mice in individual cages (20×15×15 cm) lined with wire mesh. A "climbing index", i.e., the percentage of time spent climbing during the 30-minute period following the first climb, was determined. Previous experience had indicated that this climbing index is reduced by dopamine antagonists except where the interacting drug causes a nonspecific sedation or muscular hypotonia. Apomorphine administered subcutaneously at a dosage level of 1 mg/kg caused intense and consistent climbing and provided a basis for the assessment of the effects of potential antagonists. At this dosage the climbing index was approximately 60% which served as a basis for this assessment.

In the climbing tests, the mice were pretreated with the drug to be evaluated as a dopamine atagonist by giving them intraperitoneal injections of 1, 10 or 20 mg/kg doses of the drug and then subjecting them to a subcutaneous injection of 1.0 mg/kg dose of apomorphine one hour, two days, 5 days or 7 days after the injection of the drug. Taking a climbing index of 60% for apomorphine, it was found that (—)N(2-chloroethyl)norapomorphine.HCl (NCA) reduced this index when given in 10 mg/kg doses, and greatly reduced it when given in 20 mg/kg doses. This effect was noted up to between four and five days after administration of the NCA. Responses to the apomorphine approached control levels five days after the pretreatment. Attempts to overcome the inhibition observed four hours to two days after administration of (—)N-(2-chloroethyl)norapomorphine.HCl by increasing the dose of apomorphine were made impractical by the development of stereotyped biting at the larger doses which reduced the climbing response per se.

In contrast to this ability of the (—)N-(2-chloroethyl)norapomorphine to materially reduce the climbing index, four-hour pretreatments with (—)N-(2-chloroethyl)norapocodiene.HCl or 6-[2-bis(2-chloroethyl)amino]acetyl-11-acetoxy-2-hydroxy-10-methoxy-apoporphine hemihydrate or 90-minute pretreatment with (—)N-(2-hydroxyethyl)norapomorphine.HCl, each given as 10 mg/kg subcutaneous injections, failed to modify apomorphine climbing.

Pretreatments with any of these drugs including NCA in doses of 10 mg/kg prior to apomorphine injections of 1 mg/kg failed to modify the submaximal stereotypic effect (repetitive sniffing, periodic biting and continuous biting) of the apomorphine.

In addition to the in vivo testing of the (—)N-(2-chloroethyl)norapomorphine.HCl, in vitro evaluations were made to determine the extent to which this drug could inhibit the activation of adenylate cyclase to stimulate the production of cyclic adenosine monophosphate (cAMP) in rat striatal homogenates. (—)N-(2-chloroethyl)norapomorphine.HCl (NCA) at three levels (10, 30 and 75 μmoles) was incubated for 10 minutes at 37° C. with homogenates of rat corpus striatum in a physiologic buffer and then washed free of the drug. Washed tissue, including one specimen without NCA as a control, was then incubated with zero or 50 μM of dopamine in the presence of an excess of adenosine triphosphate for 2.5 minutes at 37° and the level of cyclic adenosine monophosphate in the incubation mixture with and without dopamine was assayed by a protein binding method. The increase in cyclic adenosine monophosphate levels due to the dopamine was estimated for all conditions. The ability of the (—)N-(2-chloroethyl)norapomorphine.HCl to inhibit the actuation of adenylate cyclase is shown in Table 1.

TABLE 1

Ability of (—)N—(2-chloroethyl)norapomorphine.HCl (NCA) To Inhibit Activation of Dopamine-Sensitive Adenylate Cyclase in Rat Striatal Homogenates

| NCA (μM) | Stimulation of cAMP Production (%) | Inhibition of Adenylate Cyclase (%) |
|---|---|---|
| 0 | 100 | 0 |
| 10 | 84 | 16 |
| 30 | 44 | 56 |
| 75 | 8 | 92 |

These effects of the (—)N-(2-chloroethyl)norapomorphine.HCl on the dopamine-sensitive adenylate cyclase are similar to those of phenoxybenzamine, a alkylating drug previously found to exert an irreversible blocking action of dopamine-sensitive adenylate cyclase. (See K. G. Walton, P. Liepmann and R. J. Baldessarini, Eur. J. Pharmacol. 52: 231 (1978).)

The ability of the (—)N-(2-chloroethyl)norapomorphine.HCl to serve as a dopaminergic agent over a prolonged period, i.e., at least five days, leads to the postulation that this drug may bind chemically to the dopamine receptors rather than act as a blocking agent as do the phenathiazines, thioxanthenes and butyrophenones. This postulation was borne out by measuring the effect of the intrastriatal binding of the drug on the subsequent binding of $^3$H-N-n-propylnorapomorphine ($^3$H-NPA), a known dopamine agonist, to the striatal tissue.

In one set of experiments three types of striatal tissue were examined: (1) that taken from untreated rats as a control; (2) that taken from rats receiving 40 μg of the NCA in 4 μliters of a solvent vehicle at a rate of 1 μliter/minute in the left hemisphere; and (3) that taken from the right hemisphere subjected to 4 μliters (1 μliter/minute) of the solvent vehicle. Animals were sacrificed on days 2, 7 and 14–16 days after the intrastriatal injection; and the striata were dissected out over ice and homogenized (100 vols, w/v) in 50 mM ice cold trihydroxymethyl amine.HCl buffer (pH 7.4 at 25° C.) with a Polytron homogenizer. The homogenate was centrifuged twice (for 10 minutes at 50,000 g) at 4° C. with resuspension in fresh buffer. Final resuspension (100 vols w/v) was in trihydroxymethyl amine buffer (pH 7.4 at 37° C.) containing 0.1% ascorbic acid, 12.5 μM nialamide and 5 mM sodium ethylenediaminetetraacetate. Each assay tube contained 5 mg wet weight striatal tissue (equivalent to approximately 275 μgram protein, in a total volume of 1.1 milliliter. After incubation (15 minutes at 37° C.) with $^3$H-NPA (61 Ci/m mol, New England Nuclear), the samples were rapidly filtered under vacuum over Whatman GF/B filters and rinsed rapidly with 2×5 milliliters ice cold trihydroxymethyl amine.HCl buffer; and the bound radioactivity was determined. Specific binding was defined as the difference between $^3$H-NPA binding in the absence and presence of 10 μM of 2-amino-6-7-dihydroxytetralin (a known dopamine agonist) and under optimal conditions accounted for approximately 75% of $^3$H-NPA less than 2.0 nM, it was found that $^3$H-NPA binding sites had a density of approximately 180 fmol/mg protein.

Figure 5:
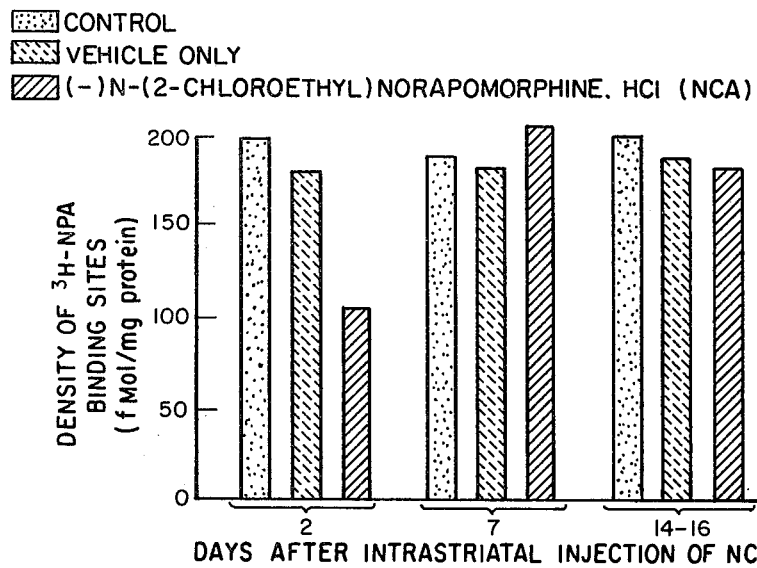
FIG. 5 is a series of bar graphs illustrating the in vivo effect of the intrastriatal binding of (N)-(2-chloroethyl)-norapomorphine.HCl on the subsequent binding of $^3$H-N-n-propylnorapomorphine.

The results of these measurements of in vivo binding are given in FIG. 5, from which it will be seen that the density of the $^3$H-NPA binding sites was essentially reduced to one-half two days after injection of the NCA. Thus these data indicate intrastriatal NCA can significantly reduce $^3$H-NPA binding and that this biochemical change follows the behavioral effects which essentially reflected "striatectomy" by NCA. Thus, on day 2, when animals showed not only an active ipsilateral circling when challenged with apomorphine but also exhibited a resting ipsilateral asymmetry (each identical to effects one would expect from striatectomy or striatal dopamine receptor blockade) the number of binding sites for the dopamine agonist $^3$H-NPA was reduced by approximately 50%. As the behavioral effects of NCA disappeared on days 7 and 14, so the number of sites available for the binding of $^3$H-NPA returned to control values. That the reduction in $^3$H-NPA binding reflects a change in receptor numbers rather than a change in affinity for the receptor sites is indicated by the constancy of values (0.88–1.12 nM) for the inhibition constant, $K_D$, for binding to striatal tissue both from control animals and those treated for various times with NCA.

Figure 6:
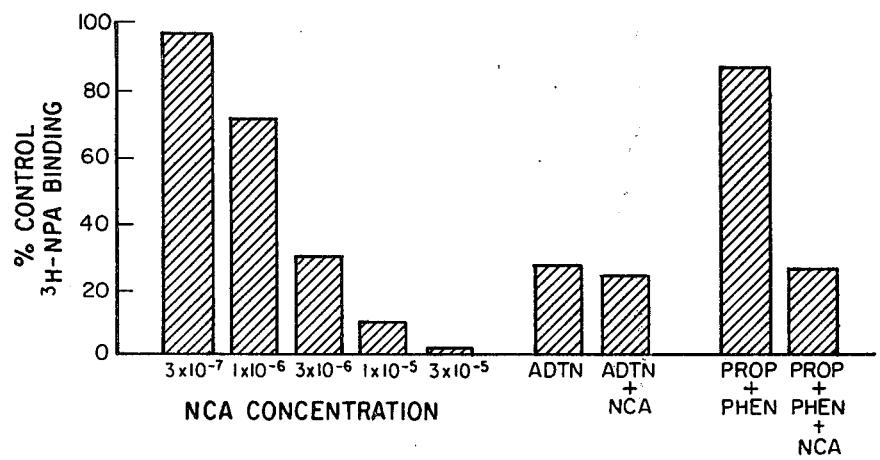
FIG. 6 is a series of bar graphs illustrating the in vitro effect of the intrastriatal binding of (N)-(2-chloroethyl)-norapomorphine on the subsequent binding of $^3$H-N-n-propylnorapomorphine alone or in the presence of other blocking agents.

The ability of (−)N-(2-chloroethyl)norapomorphine.HCl (NCA) to inhibit the binding of $^3$H-NPA was further established in in vitro experiments which facilitated an examination of the doses and conditions under which NCA could inhibit dopamine mechanisms. Incubation tubes containing rat striatal homogenate were preincubated for 2.5 minutes at 37° C. with NCA at five concentrations (3×10$^{-5}$ to 3×10$^{-7}$ M); with 2-amino-6,7-dihydroxytetralin (ADTN) with ADTN and NCA (3×10$^{-5}$ M); with propranolol (1×10$^{-6}$ M) and NCA (3×10$^{-5}$ M) prior to the addition of 0.5 nM $^3$H-NPA for incubation at 37° C. for 15 minutes. Membranes were collected by filtration and measurements were made using the same technique described above. The data obtained in terms of percent of $^3$H-NPA binding are plotted in FIG. 6. From these data it will be seen that NCA at 1.8×10$^{-6}$ M caused a 50% inhibition of $^3$H-NPA binding. Moreover, this inhibition was also apparent in the presence of high concentrations of phentolamine (an α-blocking agent) and propranolol (a β-blocking agent which could be expected to hinder occupancy of other catecholamine receptors by either $^3$H-NPA or NCA. Furthermore, the inhibition of "specific" $^3$H-NPA binding by ADTN could not be further increased by NCA, indicating that the ability of the NCA to prevent $^3$H-NPA binding does not occur at "nonspecific" sites. Finally, the prevention of $^3$H-NPA binding by NCA (10$^{-5}$ M) was not reversed by repeated washing.

Figure 8:
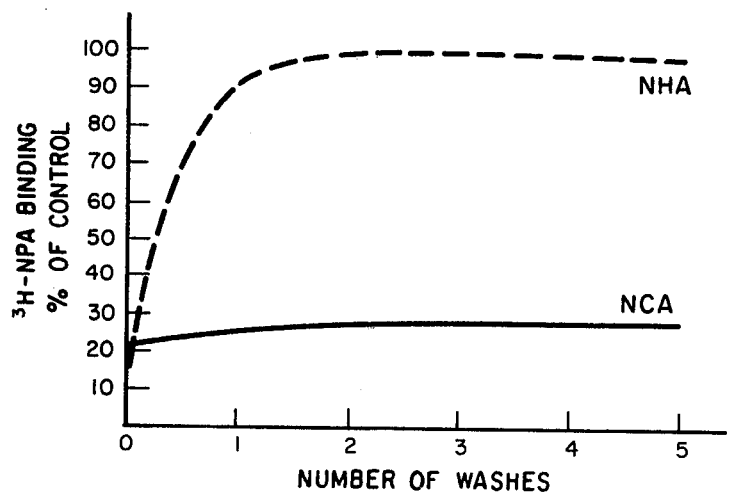
FIG. 8 illustrates, in plots, the effect of washing on the binding of (—)-N-(2-chloroethyl)norapomorphine.HCl to rat striatal homogenate.
Figure 7:
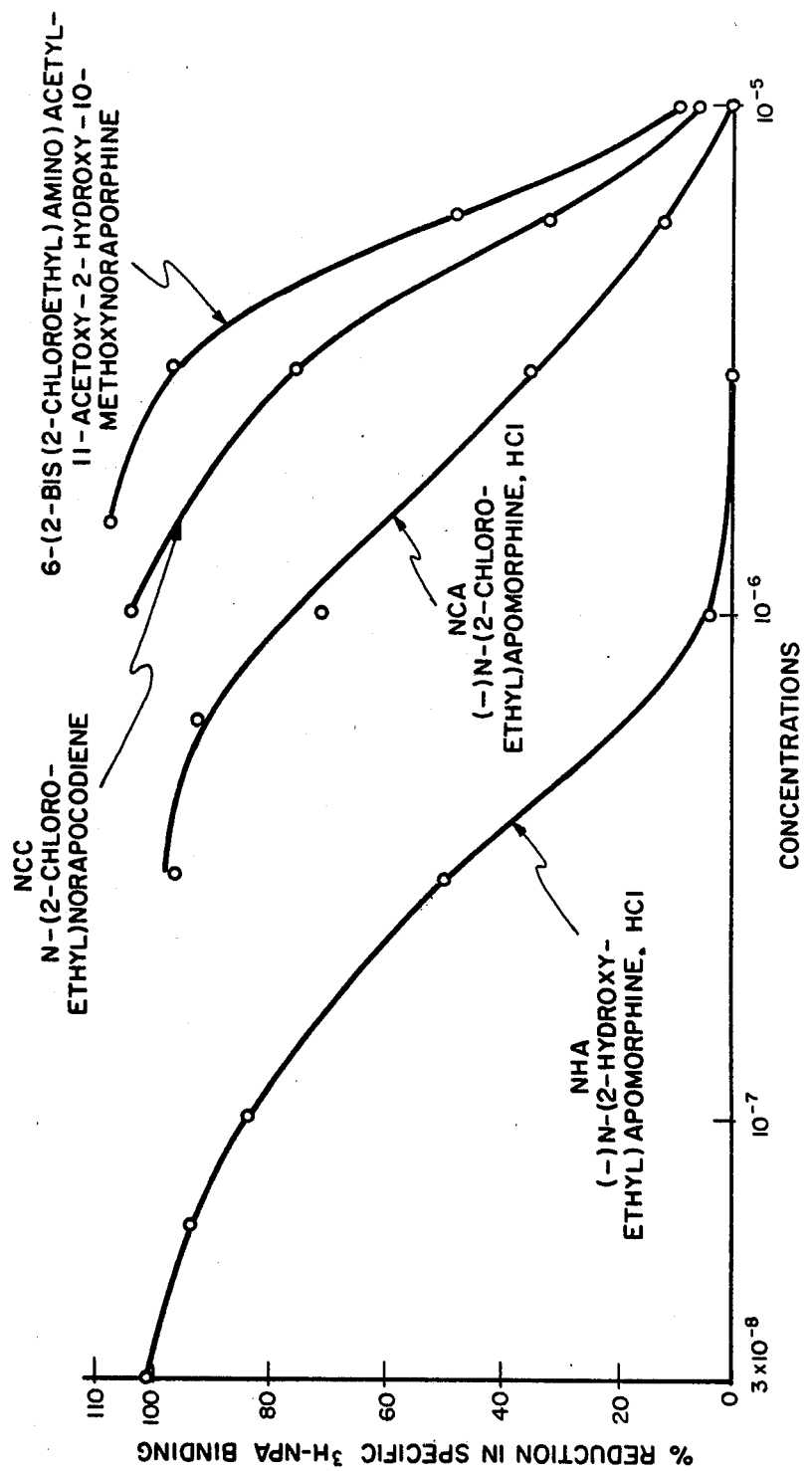
FIG. 7 is a series of plots illustrating the ability of four different apomorphine-type compounds to reduce the specific binding of $^3$H-N-n-propylnorapomorphine in rat striatal homogenate.

Using a similar technique and 10 μM of ADTN to first assess the "specific" binding of $^3$H-NPA to rat striatal homogenate, it was determined that the $^3$H-NPA bound to the striatal membranes with an inhibition constant, $K_D$, of 1.0 nM and $B_{max}$ of 190 fmol/mg protein. With this base to work with, the abilities of four aporphine derivatives to prevent the specific binding of $^3$H-NPA were determined and the results are plotted in FIG. 7. From this plot it will be seen that the NHA is a more potent binding agent at low concentrations than NCA. However, as will be seen from FIG. 8, when the incubated membranes with NCA (5×10$^{-6}$ M) or with NHA (5×10$^{-7}$ M), both of which prevented the binding of 0.125 nM $^3$H-NPA, were washed, only the inhibition provided by the NCA was not reversed. Thus it alone was capable of sustained binding to the rat striatal homogenate protein.

The in vivo data show that the (−)N-(2-chloroethyl)-norapomorphine.HCl, when administered either peripherally or intrastriatally, can effect behavioral changes indicative of changes at the receptor level associated with dopamine receptor blockade. The in vitro data further show that such inhibition is the result of binding to the receptor, a fact which may explain the prolonged action of the drug. These two properties offer the possibility of providing an improved neuroleptic drug.

It will thus be seen that the objects set forth above, among those made apparent from the preceding description, are efficiently attained, and, since certain changes may be made in carrying out the above methods and in the compounds set forth without departing from the scope of the invention, it is intended that all matter contained in the above description shall be interpreted as illustrative and not in a limiting sense.

I claim:
1. A method of inactivating dopamine receptor sites and enhancing dopaminergic activity by administering a therapeutically effective amount of a compound of the formula

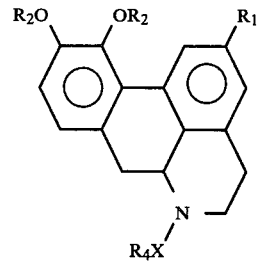

wherein $R_1$ is $R_2O$; $R_2$ is hydrogen, $C_1$ to $C_6$ alkyl or

where $R_3$ and $R_4$ are $C_1$ to $C_6$ alkyl and X is halogen and the acid addition salts thereof selected from the group formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isothionic acid, benezenesulfinic acid, p-toluenesulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydroidic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid barbituric acid and boron trifluoride.

2. The compound (—)N-(2-chloroethyl)norapomorphine and the acid addition salts thereof selected from the group formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfinic acid, p-toluenesulfonic acid, benzesulfinic acid, butylarsonic acid, diethylphosphinic acid, p-aminophenylarsinic acid, phenylstibnic acid, phenylphosphinous acid, methylphosphonic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid and boron trifluoride.

3. A method of inactivating dopamine receptor sites and enhancing dopaminergic activity by administering a therapeutically effective amount of a compound of the compound (—)N-(2-chloroethyl) norapomorphine and the acid addition salts thereof selected from the group formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isothionic acid, benzenesulfinic acid, p-toluenesulfonic acid, benzesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfiric acid, phosphoric acid, hydrocyanic acid, phosphotungstic acid, molybdic acid, phosphomolybdic acid, pyrophosphoric acid, arsenic acid, picric acid, picrolonic acid, barbituric acid and boron trifluoride.

4. A method of claim 3 wherein said acid addition salt is the hydrochloride salt.

* * * * *

UNITED STATES PATENT AND TRADEMARK OFFICE
CERTIFICATE OF CORRECTION

PATENT NO. : 4,353,912
DATED : October 12, 1982
INVENTOR(S) : John L. Neumeyer

It is certified that error appears in the above—identified patent and that said Letters Patent is hereby corrected as shown below:

Column 3, line 64, "$^3$H-N-n-" should read --H-N-n--.

Column 4, line 17, "prefered" should read --preferred--.

Column 6, line 23, "doseage" should read --dosage--;

line 43, "stratectomized" should read --striatectomized--.

Column 12, line 2, "thylphosphonic" should read --thylphosphinic--.

Signed and Sealed this

Seventh Day of May 1985

[SEAL]

Attest:

DONALD J. QUIGG

Attesting Officer

Acting Commissioner of Patents and Trademarks